(12) United States Patent
  Paulos

(10) Patent No.: US 8,814,935 B2
(45) Date of Patent: Aug. 26, 2014

(54) INTERFERENCE SCREW DRIVER ASSEMBLY AND METHOD OF USE

(75) Inventor: Lonnie Paulos, Pensacola Beach, FL (US)

(73) Assignee: The Lonnie and Shannon Paulos Trust, Salt Lake City, UT (US)

(*) Notice: Subject to any disclaimer, the term of this patent is extended or adjusted under 35 U.S.C. 154(b) by 1027 days.

(21) Appl. No.: 12/353,230

(22) Filed: Jan. 13, 2009

(65) Prior Publication Data

US 2009/0248029 A1   Oct. 1, 2009

Related U.S. Application Data

(60) Provisional application No. 61/041,222, filed on Mar. 31, 2008.

(51) Int. Cl.
| | | |
|---|---|---|
| A61F 2/02 | (2006.01) | |
| A61F 2/08 | (2006.01) | |
| B25B 23/00 | (2006.01) | |
| A61B 17/88 | (2006.01) | |
| B25B 15/02 | (2006.01) | |
| A61B 17/86 | (2006.01) | |

(52) U.S. Cl.
CPC ........... *B25B 23/0042* (2013.01); *A61F 2/0805* (2013.01); *B25B 23/0035* (2013.01); *A61B 17/8897* (2013.01); *B25B 15/02* (2013.01); *A61B 17/8645* (2013.01); *A61B 17/8875* (2013.01)
USPC ....................... 623/11.11; 623/13.11; 606/104

(58) Field of Classification Search
USPC .................... 606/104; 81/439; 623/11, 13.11
See application file for complete search history.

(56) References Cited

U.S. PATENT DOCUMENTS

| | | | | |
|---|---|---|---|---|
| 4,409,866 A | * | 10/1983 | McBride | 81/177.2 |
| 4,827,812 A | * | 5/1989 | Markovetz | 81/439 |
| 5,211,647 A | | 5/1993 | Schmieding | |
| 5,351,404 A | * | 10/1994 | Smith | 30/366 |
| 5,431,651 A | | 7/1995 | Goble | |
| 5,458,604 A | | 10/1995 | Schmieding | |
| 5,464,407 A | * | 11/1995 | McGuire | 606/86 R |
| 5,645,547 A | | 7/1997 | Coleman | |
| 5,797,918 A | | 8/1998 | McGuire et al. | |

(Continued)

OTHER PUBLICATIONS

International Bureau of the WIPO, International Preliminary Report on Patentability (IPRP) for related PCT App. No. PCT/US2009/033617, filed Feb. 10, 2009, IPRP Mailed Oct. 14, 2010, Switzerland.

(Continued)

*Primary Examiner* — Eric Rosen
(74) *Attorney, Agent, or Firm* — John Brooks Law LLC; John J Brooks, III

(57) ABSTRACT

Embodiments of the present invention provide a cannulated screw driver assembly which includes a rigid guide pin such that the assembly can be used to assist the surgeon in inserting and positioning the rigid guide pin and an interference screw within a bone graft tunnel. Once the screw is properly placed, screw driver assembly components to include the rigid guide pin, the driver and the handle can be removed while the screw remains in the tunnel to secure the graft. In one embodiment, the interference screw can be removed from the distal end of the driver and the driver and handle can be removed from the screw's proximal end. Embodiments of the inventions also include an interchangeable driver to mate with different size and types of interference screws.

21 Claims, 7 Drawing Sheets

(56) References Cited

U.S. PATENT DOCUMENTS

| | | |
|---|---|---|
| 6,544,281 B2 | 4/2003 | ElAttrache et al. |
| 7,207,995 B1 | 4/2007 | Vandewalle |
| 2002/0120275 A1 | 8/2002 | Schmieding et al. |
| 2003/0093081 A1* | 5/2003 | Hawkes ............. 606/104 |
| 2004/0102780 A1 | 5/2004 | West, Jr. |
| 2005/0222575 A1* | 10/2005 | Ciccone et al. ........ 606/104 |
| 2005/0277931 A1 | 12/2005 | Sweeney et al. |
| 2005/0283156 A1 | 12/2005 | Schmieding et al. |
| 2006/0030850 A1 | 2/2006 | Keegan et al. |
| 2006/0079894 A1 | 4/2006 | Colleran et al. |

OTHER PUBLICATIONS

Kim, Hee Seung, International Search Report and Written Opinion for co-pending PCT Application PCT/US2009/033617, mailed Aug. 27, 2009, Korean Intellectual Property Office, Korea.

* cited by examiner

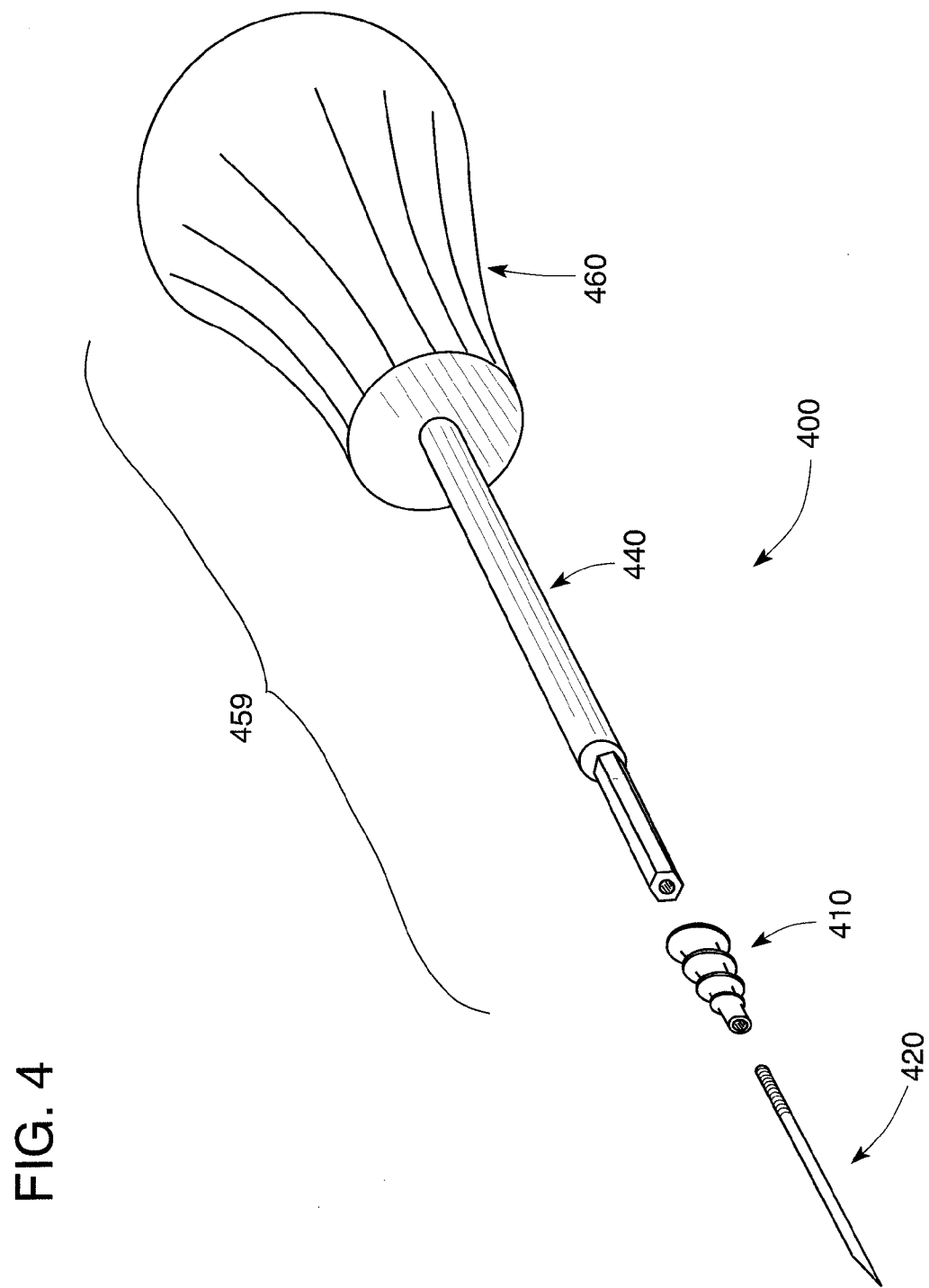

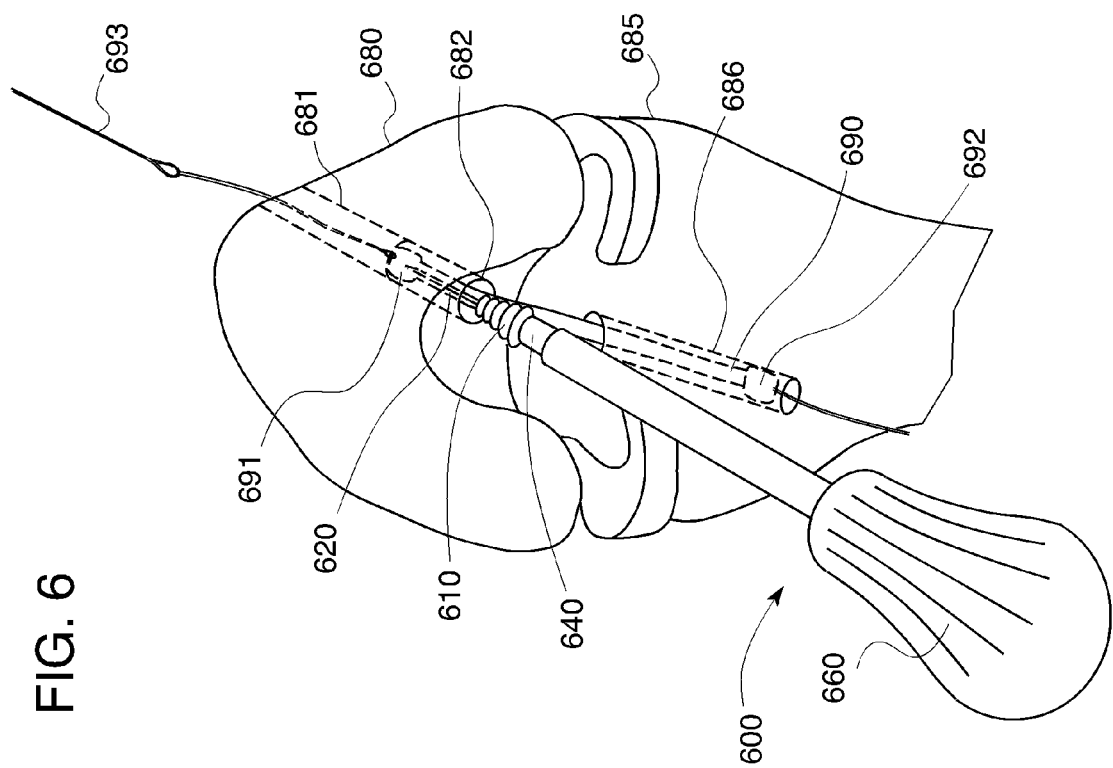

INTERFERENCE SCREW DRIVER ASSEMBLY AND METHOD OF USE

CROSS-REFERENCE TO RELATED APPLICATIONS

This application claims the benefit of the following provisional applications, each of which is hereby incorporated by reference in its entirety: U.S. Patent Application Ser. No. 61/041,222, entitled SELF-GUIDED CANNULATED SCREW DRIVER ASSEMBLY AND METHOD OF USE, filed on 31 Mar. 2008.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention relates to an interference screw driver for orthopedic surgery and, more specifically, to a self-guided screw driver which can be used with a rigid guide pin during fixation of a graft such as a ligament by insertion of an interference screw.

Description of the Related Art

In orthopedic surgery cannulated screws are used to attach plates, washers and other types of fixation devices to bone. They are also used to fix bone to bone and ligament to bone reconstructions. By using a cannulated screw, the surgeon is able to use tools such as guide wires to ensure the screw will follow the path that it is intended to travel.

Fixation of a substitute ligament or graft is well known in the art. See, U.S. Pat. No. 5,211,647 by Reinhold Schmieding which is herein incorporated by reference in its entirety. When a ligament or tendon becomes detached from a bone, surgery is usually required to resecure the ligament or tendon. Often, a substitute ligament, or graft, is attached to the bone to facilitate regrowth and permanent attachment. Various methods of graft attachment are known, such as staples and sutures over buttons. However, such methods often do not provide a sufficiently strong attachment to withstand the normal tensile loads to which they are subjected. A stronger graft attachment is obtained by using an interference screw to wedge a graft bone block to the wall of a graft tunnel formed through the bone. With these methods being used in an anterior cruciate ligament reconstruction, a graft with bone blocks at either end is pulled through a graft tunnel in the tibia by applying a tensile force on sutures attached to a leading bone block. The leading bone block is brought forward into the femur until it is fully nested in a graft tunnel in the femur. Then, with tension applied to the graft via sutures, a screw driver is used to insert interference screws between the bone block and the graft tunnel. Similar steps are applied to bone blocks in a tibial tunnel to secure the graft to the tibia.

Prior devices and methods incorporate the cannulated screw driver and cannulated screw that advance over a guide wire to help position the screw against the bone block. For example, U.S. Pat. No. 5,797,918, by David A. McGuire, which is herein incorporated by reference in its entirety, discloses a flexible screw driver for arthroscopic ligament reconstruction. However, inserting the guide wire is cumbersome, because the wire is flexible, tends to bend and is difficult to grip. Also, handling the guide wire and screw driver as separate pieces is inconvenient during surgery.

In addition, the sizing of interference screws for different surgical procedures forces different configurations of drivers to mate with the interference screw.

BRIEF DESCRIPTION OF THE SEVERAL VIEWS OF THE DRAWING

These and other features of the present invention may be more readily understood by reference to the following description, taken in conjunction with the accompanying drawings:

FIG. 4. An exploded side view of one embodiment of the screw driver assembly showing its interaction with an interference screw.

FIG. 6. A front view of one embodiment of the methods of the invention anchoring a screw and a ligament in a femoral tunnel.

SUMMARY

Figure 1:
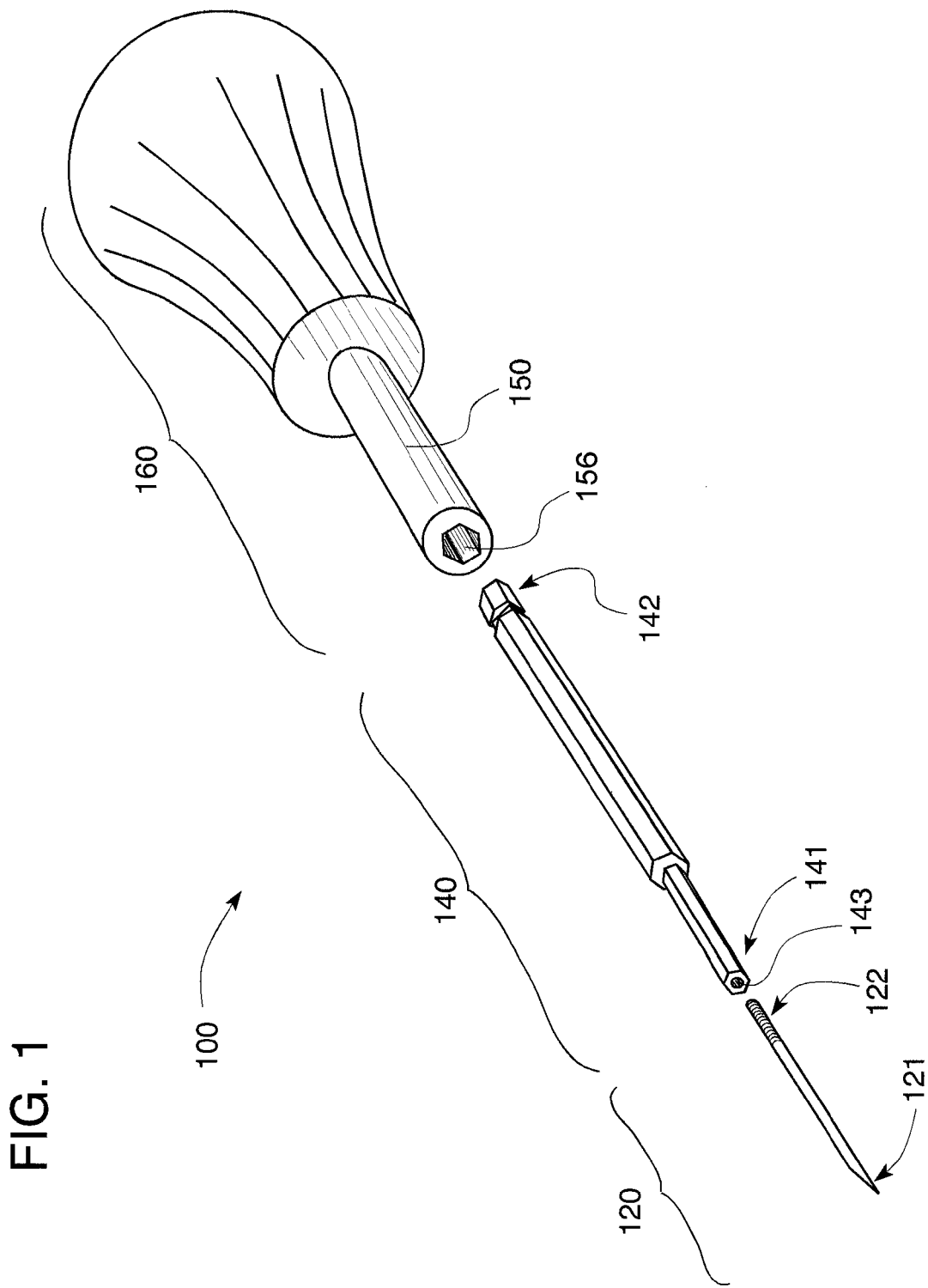
FIG. 1. An exploded side perspective view of one embodiment of the screw driver assembly.

The present invention overcomes the deficiencies of the prior art by providing a cannulated screw driver assembly which includes a rigid guide pin such that the assembly can be used to assist the surgeon in inserting and positioning the guide pin and the interference screw within a graft tunnel. Once the screw is properly placed, screw driver assembly components of assembly include the guide pin, a driver and a handle that can be removed while the screw remains in the tunnel to secure the tissue. In one embodiment, the interference screw can be removed from the distal end of the driver and the driver and handle can be removed from the screw's proximal end. Embodiments of the inventions also include an interchangeable driver to mate with different size and types of interference screws.

Embodiments of the disclosed assemblies and methods of use recognize that prior art angled surgical drivers are unsuitable for use in some surgeries where the procedures can benefit from the ability to put a larger amount, and a more direct, force behind the interference screw. Embodiments have the longitudinal axes of the assembly components being aligned, whereby a more direct force is able to be transferred from the handle of the assembly to the guide pin and the interference screw. This allows for more control of the assembly, ensures the proper engagement of the screw with the tissue and the bone and lowers the possibility of damaging surrounding tissue.

Embodiments also recognize that a rigid guide pin is able to advance with the screw, making the guide pin more difficult to bend or break than traditional guide wires.

One embodiment of the invention comprises an interference screw driver assembly for use with an interference screw in surgery, the screw driver assembly comprising: a rigid guide pin having a proximal end and a distal end, a driver having a proximal end and a distal end, a pin connection means to connect the rigid guide pin to the driver and a handle having a handle connection means to removably connect the driver to the handle whereby the rigid guide pin can be guided into position by positioning the rigid guide pin through manipulation of the handle.

In another embodiment of the invention, the interference screw driver assembly comprises the driver distal end having a threaded recess and the rigid guide pin proximal end having threads whereby the threads of the rigid guide pin proximal end are received and mate with the threaded recess of the driver distal end to connect the rigid guide pin with the driver.

In yet another embodiment of the invention, the interference screw driver assembly comprises: the handle having a proximal end, a distal end and a longitudinal axis, and the distal end of the handle having a recess shaped to receive the proximal end of the driver whereby a rotation of the handle about the longitudinal axis turns the guide pin and the driver about the longitudinal axis.

In one embodiment of the invention, the interference screw driver assembly further comprises a plurality of drivers, the plurality of drivers having different shaped distal ends whereby the driver can be interchanged so that the driver distal end can mate to a plurality of interference screws and a rotation of the handle about the longitudinal axis turns the shaft, the rigid guide pin, the driver and the interference screw about the longitudinal axis.

In another embodiment of the invention, the interference screw driver assembly is capable of anchoring an interference screw and a ligament in bone.

In one embodiment of the invention, the interference screw driver assembly comprises a rigid guide pin having a proximal end and a distal end, a driver having a proximal end and a distal end, a pin connection means to connect the rigid guide pin to the driver, an interference screw having a longitudinal bore whereby at least a portion of the rigid guide pin and the driver can be received in the screw longitudinal bore, and a handle having a handle connection means to removably connect the driver to the handle whereby the rigid guide pin and the interference screw can be guided into position for surgery by manipulation of the handle.

In another embodiment of the invention, the interference screw driver assembly comprises an interference screw having a having a proximal end and a distal end, the rigid guide pin having an outside diameter, the driver having an outside profile, the screw distal end having a longitudinal bore size slightly larger than the outside diameter of the rigid guide pin, the screw distal end having a longitudinal bore size slightly larger than the driver outside profile whereby the proximal end of the rigid guide pin can be received in the longitudinal bore of the screw distal end, the distal end of the driver can be received in the longitudinal bore of the screw proximal end, and the pin connection means connect the rigid guide pin to the driver.

In yet another embodiment of the interference screw driver assembly, the screw driver assembly further comprises a plurality of drivers, the plurality of drivers having different shaped distal ends whereby the driver distal end removably mates to a plurality of interference screws and a rotation of the handle about the longitudinal axis turns the shaft, the rigid guide pin, the driver and the interference screw about the longitudinal axis.

One embodiment of the present invention comprises a method of deploying an interference screw comprising the steps of connecting a proximal end of a driver to a distal end of a handle, connecting a proximal end of a rigid guide pin to a distal end of the driver, inserting the driver and the rigid guide pin into a longitudinal bore in an interference screw, driving the rigid guide pin and the screw between a graft and a tissue of a patient by manipulating the handle, and removing the driver and the rigid guide pin from the screw whereby the interference screw anchors the graft to the tissue.

Another embodiment of the present invention comprises the method of deploying an interference screw wherein the graft is a previously cut bone block and the tissue is a bone mass having a graft tunnel.

A further embodiment of the present invention comprises the method of deploying an interference screw wherein the rigid guide pin proximal end is threaded and connected to a threaded recess in the driver distal end, and wherein the rigid guide pin is removed from the driver by rotating the rigid guide pin out of the driver and the driver is removed from the interference screw by applying a retrograde force to the driver.

Yet another embodiment of the present invention comprises the method of deploying an interference screw wherein the step of connecting the proximal end of the driver to the handle further comprises selecting the driver from a plurality of drivers, and the plurality of drivers having different shaped distal ends whereby the driver distal end removably mates to a plurality of interference screws.

DETAILED DESCRIPTION OF THE INVENTION

An interference screw driver assembly and methods for use will now be described in detail with reference to the accompanying drawings. Although embodiments are described for the anchoring of devices and tissues to bone and other tissues, it is understood that the methods and systems described can be use for use in other medical attachment procedures. Notwithstanding the specific example embodiments set forth below, all such variations and modifications that would be envisioned by one of ordinary skill in the art are intended to fall within the scope of this disclosure.

Screw Driver Assembly:

As shown in FIG. 1, one embodiment of the screw driver assembly 100 comprises a rigid guide pin 120, a driver 140 and a handle 160.

The rigid guide pin 120 is an elongated element made from a material such as titanium, stainless steel, nitinol or a nickel-titanium alloy wire. The guide pin can be of any length, but is typically on the order of 0.70-8 inches or more preferably 1-2.5 inches in length. In one embodiment, the rigid guide pin 120 has a sharpened distal end 121 and a threaded proximal end 122. The sharpened distal end 121 helps the guide pin penetrate tissue, bone or spaces therebetween and the threaded proximal 122 end provides the pin connection means to connect the rigid guide pin to the driver 140. The guide pin is generally designed to be rigid. For example and not for limitation, with a cylindrical implementation of the guide pin made of nitinol, a diameter range of 0.09-0.035 inches for the pin is suitable to ensure the proper rigidity. Additionally, for the nitinol example, a diameter range of 0.08-0.045 inches is suitable to ensure rigidity and a diameter range of 0.067-0.057 is preferred. Although this embodiment has a threaded proximal end, other means of removably connecting the guide pin to the driver are suitable such as pins, clips, friction or other removable connection methods.

Because there are many different applications for this assembly, embodiments of the rigid guide pin 120 can comprise multiple guide pins of differing lengths, rigidity or diameter. It is also understood, that single length guide pins of a longer length can be provided that can be cut to the required length. It is also contemplated that in some embodiments, the pin can be integral or otherwise permanently connected to the driver. By having a consistent means of connecting the guide pins to the driver, these pins can be interchanged as needed for the different applications.

The driver 140 has a proximal 142 and a distal end 141. The distal end 141 is shaped to fit into a portion of the bore of an interference screw (one embodiment shown in FIG. 5) so that it does not slip rotationally within the screw bore. The means to receive the driver 140 into the screw is through the longitudinal bore in the screw that is complementary shaped to receive the distal end of the driver. In the embodiment shown in FIG. 1, and not for limitation, the means to receive is a hexagonal bore in the screw that mates with a hexagonal outside profile of the distal end 141 of the driver. Other shapes of the driver distal end 141 are possible such as but not limited to square head, philips head, star shaped, square or any other shape that will provide a removable connection to the screw while still providing the ability to rotationally engage the screw. When received into the screw, the driver 140 can be rotated about its longitudinal axis which in turn rotates the screw about its longitudinal axis.

Because there are multiple shapes, sizes and screw configurations that can be used with this assembly, embodiments of this system can include various interchangeable drivers or driver attachments of which the proximal end will be shaped to match present day cannulated screw systems. Most systems require a hex head screw driver end while others require triangular or square screw driver head end. All of these shapes as well as others can be accommodated with various choices in the self guided screw driver assembly.

The driver distal end 141 has a means to receive the proximal end of the guide pin. In one embodiment, the driver distal end 141 also has a threaded recess 143 to receive a threaded guide pin 120. When the driver 140 is received in a cannulated screw and the guide pin 120 is connected to the driver 140, only a portion of guide pin 120 is in the screw and another portion of the guide pin 120 extends outside of the pointed distal end of the screw. Other means of attaching the guide pin to the driver are contemplated such as pins, clips, friction or other removable connection methods that will mate with the guide pin.

The driver proximal end 142 is shaped to be received and removably connected to the handle 160 so that it can be rotated with the handle 160 without slipping rotationally. In the embodiment shown in FIG. 1, and not for limitation, one means to connect the driver to the handle is the driver having a hex-shaped proximal end 142 to fit into a complementary shaped hex-shaped recess or bore 156 in the handle. Other shapes of the driver 140 are possible so that the driver will removably fit securely in the handle 160 and the screw. Although not required, the driver also has a locking means, such as a locking bearing, clip or ball detent that is capable of removably locking the driver into the handle recess.

The driver 140 is preferably made of titanium or stainless steel, although other hard metals, composites and plastics may be used, such as but not limited to titanium alloys, stainless steel alloys and material specially tailored for hardness, tensile strength and compressive strength. The shape of the driver is generally elongated and with a circumference small enough to allow the driver to be inserted at least partially into portals, incisions and tunnels in which this assembly will be used.

The handle 160 is used to manipulate the assembly and advance the screw into bone or tissue. The handle 160 has a handle connection means to removably connect the driver 140 to the handle 160. In one embodiment, this means comprises the handle having a shaft 150 with the handle recess 156 being in the distal end of the shaft 150 to receive the driver 140. Other means of connecting the driver 140 to the handle 160 are suitable such as mating threads, pins, clips, friction or other removable connection methods. The handle 160 is shaped to enable the user to put a longitudinal and rotational force on the handle and other elements attached to the handle. The handle 160 and shaft 150 are preferably made of titanium or stainless steel, although other hard metals, composites and plastics may be used, such as but not limited to titanium alloys, stainless steel alloys and material specially tailored for hardness, tensile strength and compressive strength.

Figure 2:
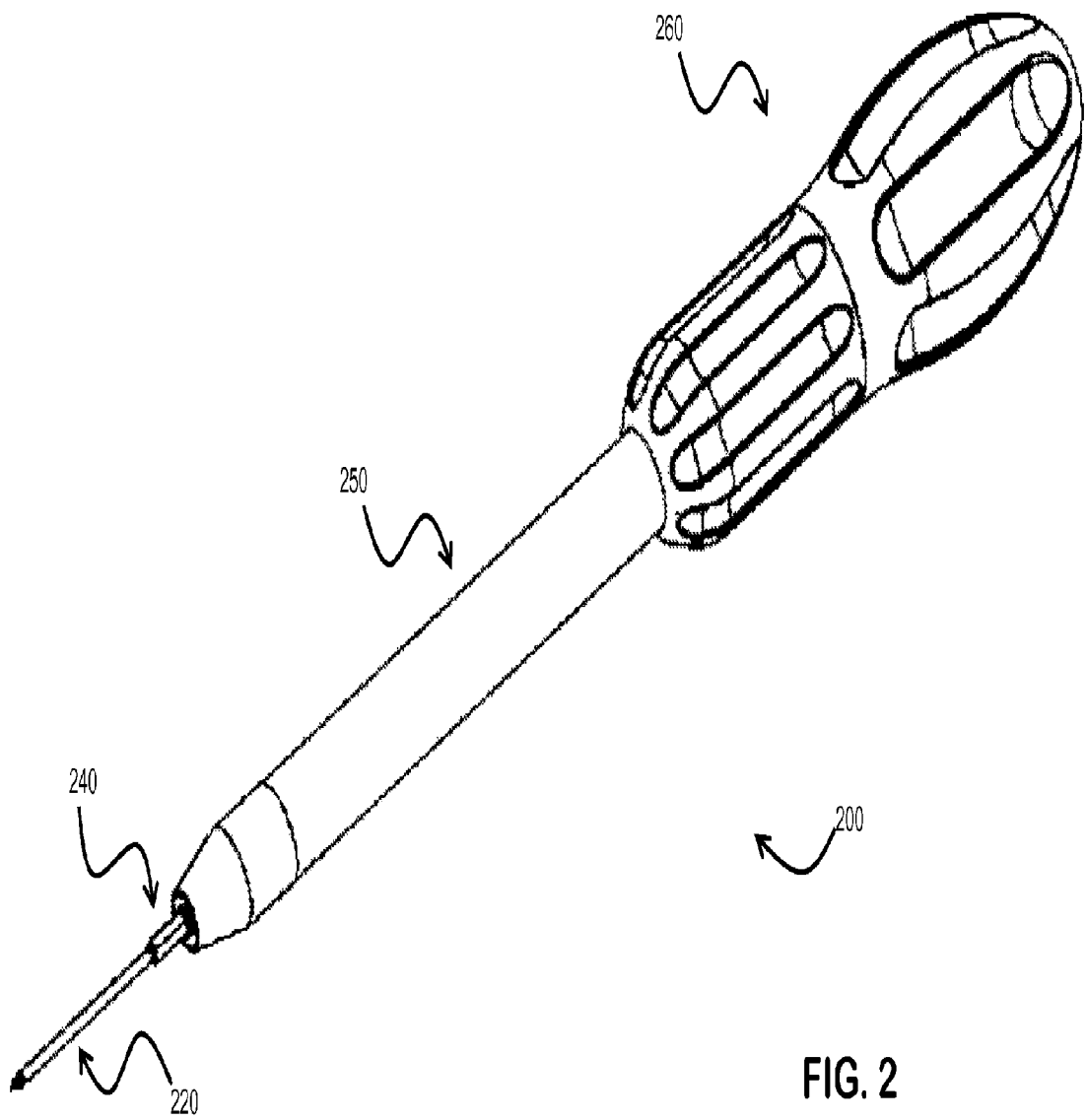
FIG. 2. A side perspective view of one embodiment of the screw driver assembly.
Figure 3:
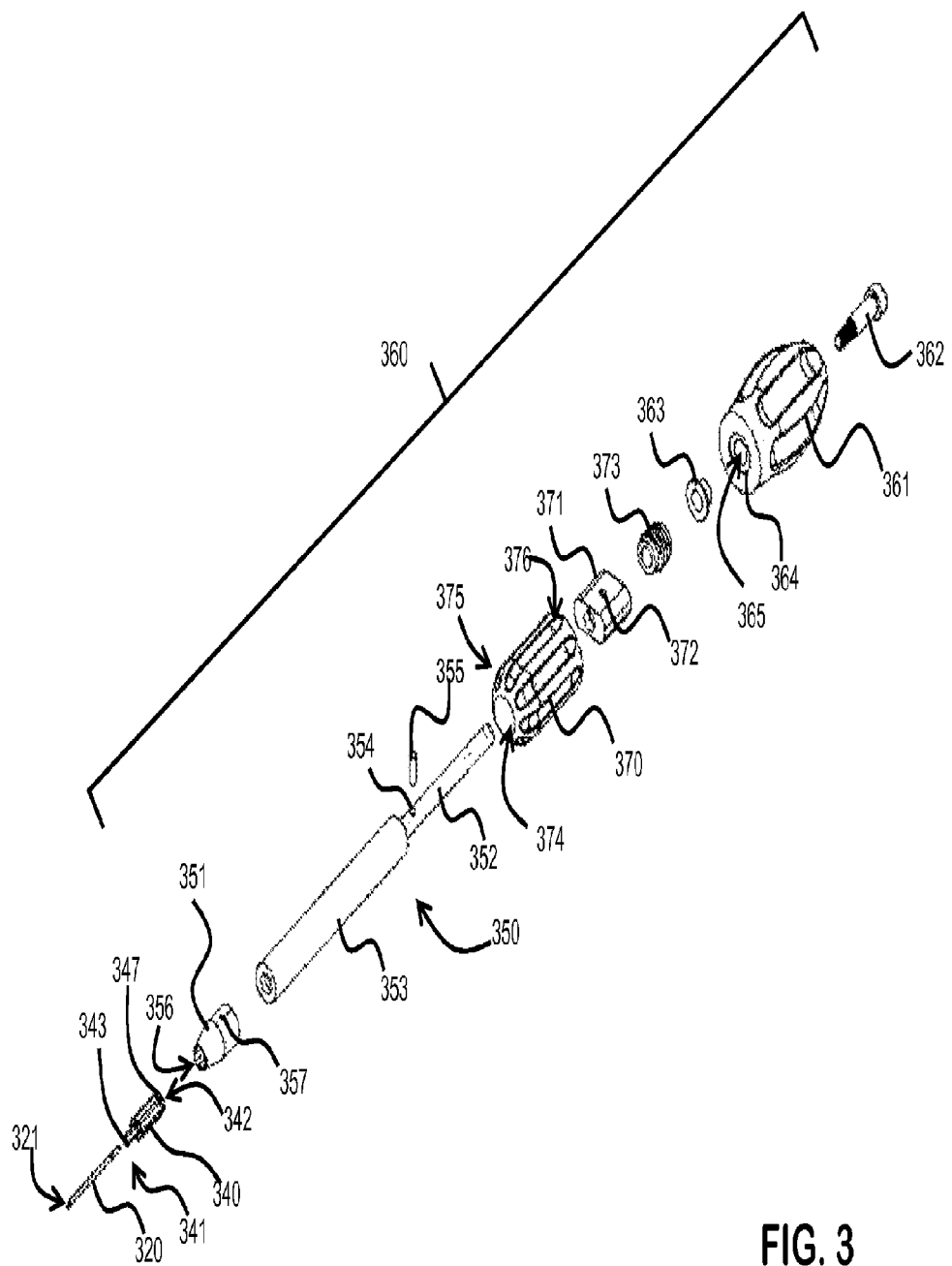
FIG. 3. An exploded side perspective view of one embodiment of the screw driver assembly.

Another embodiment of the screw driver assembly is shown assembled in FIG. 2. Similar to the embodiment of FIG. 1, the screw driver assembly 200 comprises a rigid guide pin 220, a driver 240 and a handle 260 having a shaft 250. FIG. 3 illustrated an exploded view of the embodiment shown in FIG. 2. As shown in these embodiments, when the guide pin, driver and handle are connected, the assembly has a consistent longitudinal axis where the longitudinal axis of the handle aligns with a longitudinal axis of the driver and a longitudinal axis of the rigid guide pin.

FIG. 3 illustrates an exploded view of an embodiment of the screw driver assembly 300 where the driver 340 has a driver distal end 341 with a bore 343 to receive the threaded end of the rigid guide pin 320. The distal end 341 is also shaped about its circumference to fit into a recess in an interference screw. In this embodiment, the distal end 341 outer shape is hexagonal to mate with a hexagonal recess in a screw. Any shape that mates with the screw, to allow the screw to be rotated is suitable. The driver proximal end 342 is shaped to be securely received in the handle 360.

In the embodiment shown in FIG. 3, the driver 340 can perform the functions of an interchangeable driver. In this case, the driver 340 can be easily removed and allows different drivers with different shaped distal ends 341 to be used while maintaining a consistent dimension and shape on the driver's proximal end 342. This allows for a simple replacement of the driver 340 for different shaped and sized screws while the remainder of the assembly 300 can stay consistent.

FIG. 3 shows the handle 360 comprising a shaft 350, a fore handle 370, a retainer 371, a joiner 373, a handle washer 363, a rear handle 361 and a shoulder bolt 362.

In this embodiment, the shaft 350 connects the driver 340 to the rest of the handle 360. The shaft 350 comprises a cap 351, a fore shaft portion 353, a rear shaft portion 352, a locking pin 355 and a pin hole 354. The cap 351 has a bore 356 that receives the driver proximal end 342 so that it mates with the driver 340 and allows it to be rotated when the cap 351 rotates. In the embodiment shown, the driver 340 has a circumferential channel 347 in its distal end that mates with a spring loaded ball detent (not shown) in the cap 351 that hold the driver 340 in the cap 351. The cap 351 is secured in the distal end of the shaft 350. The shaft 350 is rigid having a generally cylindrical shape. The fore shaft 353 has an outer circumference slightly larger than the circumference of the rear shaft 352. The rear shaft 352 has a pin hole 354 that receives a locking pin 355. The pin hole 354 extends perpendicular to the longitudinal axis of the shaft 350. The shape of the pin hole 354 and the locking pin 355 allows the pin to only be received partially by the hole. This allows a portion of the locking pin 355 to extend outside of the shaft 350 and engage the shaft retainer pin hole 354.

The ball detent in the cap 351 is one method of retaining the driver 340 in the cap bore 356. In this embodiment, the ball detent is a ball bearing retained in a channel 357 (only partially shown) within the cap. By design, the ball bearing protrudes into the bore 356 by the force of a spring. When the driver's proximal end 342 is inserted into the bore 356, the ball bearing is forced into the channel 357 and out of the bore so that the proximal end 342 can proceed into the bore 356. When the driver channel 347 of the proximal end 342 is adjacent to the ball bearing, the spring forces the bearing out into the channel 347. This provides a method of retaining the driver 340 in the bore 356. When it is desired to remove the driver 340, a retrograde force is placed on the driver 340 and the ball bearing again gives way to let the driver 340 be pulled from the bore 356. Other methods of retaining the driver in the bore include but are not limited to springs, mating clips, threads, channels or permanent adhesives.

The fore handle 370 provides a surface that can be easily gripped by the user and secures the shaft 350 to the assembly. The fore handle 370 has a bore 374 extending from a distal end 375 to a proximal end 376. The fore handle bore 374 in its distal end is shaped to receive the rear shaft 352 of the shaft 350. At the fore handle's proximal end 376, the bore 374 is shaped to receive the rear shaft 352, the shaft retainer 371 and the joiner 373. The shape of the bore at the proximal end receives the shaft retainer 371 while preventing the retainer 371 and shaft 350 from rotating about the assembly's 300 longitudinal axis. The proximal end of the fore handle 370 is also shaped to receive the joiner 373. When inserted in this embodiment, the joiner 373 retains the retainer 371 in the fore handle 370. The shaft retainer 371 and the joiner 373 also have a longitudinal bore shaped to receive the rear shaft 352 when it is inserted through the fore handle 370. In this embodiment, the retainer 371 has an oblong shape that is received in a mating oblong recess in the fore handle 370. The recess in the retainer 371 is cylindrical to receive the rear shaft 352. The retainer 371 also has a locking pin hole 372 to allow the locking pin 355 to be inserted through the fore handle 370, the retainer 371 and through the rear shaft pin hole 354 to restrain the rear shaft 352 in the retainer 371 and the fore handle 370. The joiner 373 has external threads about its circumference to mate with a threaded portion of the fore handle bore.

The rear handle 361 also provides a surface for the user to manipulate the assembly. In this embodiment, the rear handle 361 has a longitudinal bore 365 and a distal end of the rear handle bore 365 is shaped to receive the handle washer 363 A portion of the bore 365 has a washer seat 364 to hold a lip of the washer 363. The handle washer 363 is received in the rear handle bore before the joiner 373 is received. The rear handle 361 also had a shoulder bolt 362 that is received in a proximal end of the rear handle bore 365. When received in the rear handle, the shoulder bolt 362 extends through the bore, through the washer 363 and the joiner 373 into a threaded recess in the rear shaft 352 whereby the rear handle 361 is able to rotate about the fore handle 370.

When this embodiment is assembled for operation, the threaded guide pin 320 is threaded and screws into the driver distal end 341. In one embodiment, the guide pin 320 screws into the driver distal end 341 for approximately 2 cm. The driver proximal end 342 is inserted into the cap 351 which is connected to the shaft 350 that is secured in the handle 360. The resulting assembly 300 allows all of the assembly elements to be manipulated by the user manipulating the handle 360. A cannulated interference screw can receive the guide pin 320 and the driver 340 so that the guide pin's distal end 321 protrudes out of the screw's pointed end and the screw can also be manipulated by the handle 360. With the screw received on the driver, the guide pin 320 guides the screw and a rotation of the handle 360 rotates the screw so that it can engage tissues in a surgical procedure. Having the two handle portions rotate about each other allows the user to provide a forward force on the rear handle 361 without rotating the screw and when in proper position, a rotational force can be applied to the fore handle 370 turning the screw.

An alternative embodiment is shown in FIG. 4 and comprises a two-piece system comprising a guide pin 420 and a combined handle and driver 459. In this embodiment, the driver 440 and the handle 460 have been combined into one element. This FIG. 4 also shows the interference screw 410 positioned to accept the guide pin and the driver 440.

Figure 5B:
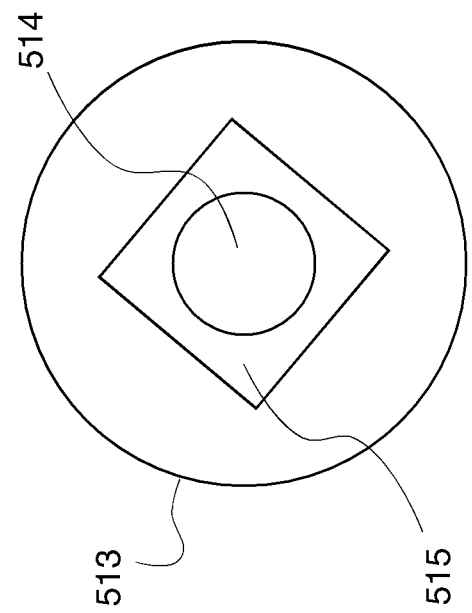
FIGS. 5A and 5B. A side view and an end view of one embodiment of a suitable interference screw to be used with embodiments of the screw driver assembly.
Figure 5A:
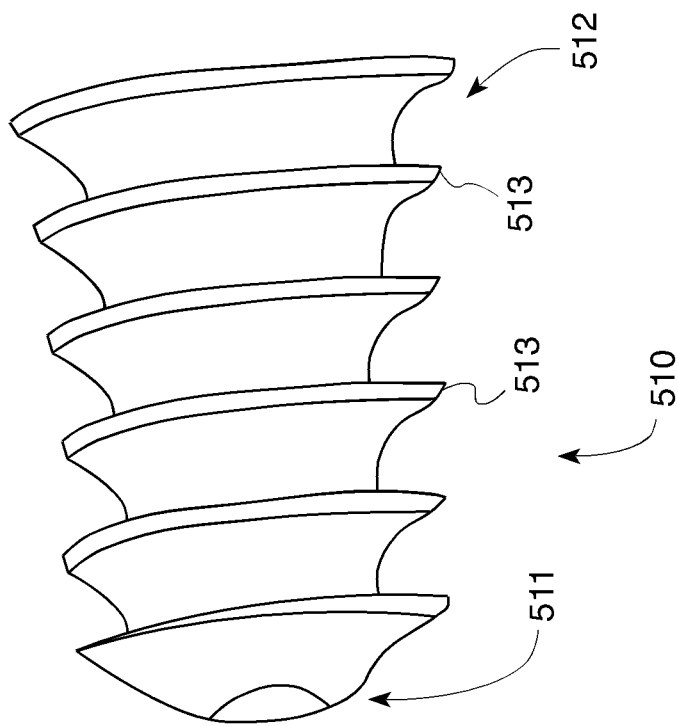

The Interference Screw:

FIGS. 5A and 5B illustrate one embodiment of a suitable interference screw 510 for use with one embodiment of this invention. FIG. 5A shows a side view of one embodiment of a screw and FIG. 5B shows a rear view. Common interference screws with longitudinal bores can be used with embodiments of this invention. The interference screw 510 is generally, but not necessarily, tapered having a pointed distal end 511, an opposite proximal end 512 and threads 513 about its exterior to secure the screw into bone and/or tissue. The screw is also has a longitudinal bore 514 between its distal 511 and proximal end 512 that is shaped to receive the driver and the guide pin. When received into the distal end of the screw, a threaded guide pin extends outside of the pointed distal end of the screw. The proximal end of the screw has a recess shaped to receive the distal end of the driver. As shown in FIG. 5, this screw recess 515 is shaped differently than the rest of the bore 514 and is shaped in this embodiment as a square to receive a square driver distal end 341. The screw is preferably made of titanium, although other hard metals, composites and plastics may be used, such as but not limited to titanium alloys, stainless steel alloys and certain biodegradable material specially tailored for hardness, tensile strength and compressive strength. The shape of the recess 515 can generally be of any shape that allows it to mate with the driver that allows the driver to translate a rotational force from the handle to the screw.

One Embodiment of the Screw Driver Assembly in Operation:

In operation, the assembly is useful in surgery that requires anchoring tissue, such as a graft ligament, to another tissue or bone. By manipulating the handle and the assembly, the self-guided screw driver advances with the interference screw into a tunnel and/or hole and the protruding guide pin proceeds in front of the screw. Because this guide pin is stronger and less flexible than guide wires, it will find its way through the tunnel or create a hole on the opposite side of a hollow bone while still positioning the screw and guiding its advancement. The removable connections of assembly provide flexibility in the assembly's manufacture and use. In addition, the ability of having a removable driver, with several drive tip sizes and shapes, allows the assembly to be used with several types and sizes of interference screws.

Figure 7:
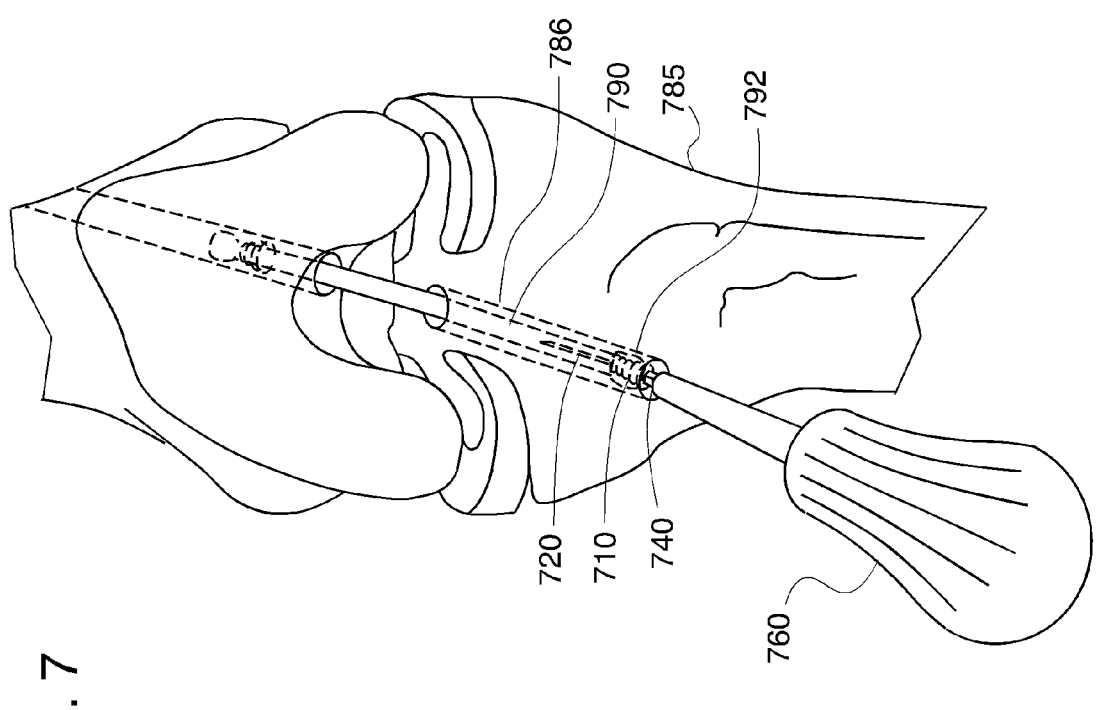
FIG. 7. A front view of one embodiment of the methods of the invention anchoring a screw and a ligament in a tibial tunnel.

For illustration purposes and not for limitation, the operation of one embodiment of the assembly will be described as used in anterior cruciate ligament reconstruction surgery as shown in FIGS. 6 and 7. With this method, an incision or puncture wound of minimal size is made to harvest a portion of the patellar tendon which will serve as a graft ligament. Subsequently, this incision can be utilized as the portal for inserting surgical instruments to fix one end of the graft ligament in the femoral bone tunnel as described below, and may also be used for access to the region of the cruciate ligament attachment sites to help determine proper placement of the tibial and femoral bone tunnels, with the knee being visualized with an arthroscope.

As shown in FIG. 6, tibial bone tunnel 686 and femoral bone tunnels 681 are formed respectively in the tibia 685 and femur 680. The femoral bone tunnel 681 is formed by instruments inserted in a cephalad direction through the tibial bone tunnel 686. The femoral bone tunnel 681 is formed as an open-ended longitudinally straight, cylindrical tunnel extending from an opening 682 on the femoral condyle at the attachment site of the anterior cruciate ligament on the femur to an opening on the lateral femoral cortex with (in one embodiment of the method) the soft tissue covering the lateral femoral cortex remaining intact.

A graft, or ligament 690, such as a prosthetic ligament or the graft ligament harvested as previously described, having bone blocks 691 and 692 or other suitable terminus at its ends, is inserted initially through the tibial bone tunnel 686 and into the femoral bone tunnel 681 via a puncture wound. (The puncture wound is in line with opening on the lateral femoral cortex and forward proximally and laterally on the patient's thigh.) A rigid pushing rod may be used to help push the graft through the tibial tunnel and into the femoral tunnel 681. A needle 693 and suture may also be used to guide the graft through the tunnels. The ligament 690 is then positioned so as to extend across the knee joint with a bone block or other terminus positioned in each of the bone tunnels in the tibial and femoral bones.

The screw driver assembly 600 as described herein is provided and assembled by connecting the driver 640 to the handle 660 and connecting the pin 620 to the driver 640. Once assembled, the driver 640 and the guide pin 620 are inserted into the bore of an interference screw 610. It is understood that some of these steps can be rearranged while still providing the same operational benefits of the invention. For example, and not for limitation, the guide pin 620 may be connected after the driver 640 is inserted in the screw 610.

With the knee at an angle of substantially 90°, the guide pin 620 of the screw driver assembly 600 is inserted at the knee joint via the incision or a separate puncture wound. The guide pin 620 is inserted through the incision and positioned into the femoral tunnel 681 alongside the bone block 691 attached to the ligament 690. The assembly 600 is guided into the femoral bone tunnel 681 through the opening on the femoral condyle 682 by simultaneously turning and pushing the handle 660. The guide pin 620 is used to position and guide the interference screw 610 to the bone block 691 at the end of the graft ligament 690 for the purposes of securing the ligament 690 with the screw 610. The screw driver assembly 600, as guided by the guide pin 620 is driven forward along the femoral bone tunnel 681, with the longitudinal axis of the assembly disposed parallel with the longitudinal axis of the femoral bone tunnel 681; and, concurrently, the guide pin 620 is driven into the tunnel.

Once the tip of the interference screw 610 is disposed adjacent the bone block 691, the handle 660 of the screw driver assembly is rotated to rotate the driver 640 relative to the bone tunnel 681. Consequently, the driver 640, driven by handle 660, drives the interference screw 610 in a forward direction in the femoral bone tunnel 681 laterally between the bone block 691 and the wall of the tunnel 681 and parallel to the bone block 691 and the tunnel wall. A thread on the screw 610 engages the tunnel wall and the bone block 691 along the length of the bone block 691 to fixate the ligament 690. The interference screw 610 is driven into the tunnel 681 far enough to countersink it below the surface of the tunnel opening 682.

The screw driver assembly 600 is then pulled away from the interference screw 610 for removal through the puncture wound. The guide pin 620 can be removed with the driver 640 or the guide pin 620 can be disconnected from the driver 640 for removal via the puncture wound in the soft tissue adjacent the lateral femoral cortex. At this point, the interference screw 610 is in place in the femoral tunnel 681 and the guide pin 620, driver 640 and handle 660 are no longer present in the patient.

The knee is then repositioned to allow the bone block 692 in the tibial bone tunnel 686 to be anchored. Usually, but not always, this repositioning is a full extension of the knee.

As shown in FIG. 7, after putting proper tension on the ligament 790 and positioning the bone block 792, the bone block in the tibial tunnel 786 is fixated by inserting a bone screw 710 in the tibial bone tunnel 786 and driving the bone screw 710 parallel to the bone block 792 and a wall of the tibial bone tunnel 786. As described above for the securing of the femoral bone block, the securing of the tibial block 792 is assisted by the positioning of the screw 710 by the guide pin 720 attached to the driver 740 and the handle 760. When the screw 710 is properly secured, the pin 720, driver 740 and handle 760 are removed.

In one embodiment of this method, if it is necessary to utilize different interference screw types or sizes, with different shaped bores, the embodiment of the assembly having multiple drivers with multiple shaped distal ends can be used. If different shaped driver ends are needed, the proper shaped driver can be selected so that it mates with each of the necessary interference screws. The same handle can be used by interchanging the drivers.

It will be appreciated that the portal can be the same incision and/or puncture wound utilized for alignment determination in forming the tibial and femoral bone tunnels, and that a single portal can be used throughout the procedure to harvest the patellar tendon graft, to orient the tibial and femoral bone tunnels, to help orient the graft ligament, and to insert the bone screw in the femoral bone tunnel.

It is also contemplated to have embodiments where the driver and the guide pin may be removed from the interference screw without removing the guide pin from the driver.

A related embodiment of the method of arthroscopic, anterior cruciate ligament reconstruction comprises the femoral bone tunnel being formed as a blind, or closed-ended tunnel extending from an opening on the femoral condyle to an end wall such that the femoral bone tunnel does not broach the lateral femoral cortex.

Other Embodiments of the Screw Driver Assembly in Operation:

It is also contemplated that the assembly can be used for other surgical procedures involving the need for rigidly attaching a tissue to bone. In particular, other procedures that benefit from the disclosed assembly and methods are those that benefit from the positioning of the rigid guide pin or the ability of the guide pin to be able to create its own tunnel through bone. Examples of these others procedures include, but are not limited to: repair and reattachment of ligaments in the shoulder such as the glenohumeral ligament, the coracohumeral ligament, the transverse humeral ligament and the coracoacromial ligament; repair and reattachment of ligaments in the elbow such as the ulnar collateral ligament; and repair and reattachment of ligament in the ankle such as the anterior talofibular ligament, the calcaneofibular ligament and the posterior talofibular ligament.

The examples above are for illustrative purpose only, as the present invention is not limited to any type of ligament replacement or tissue attachment to bone. Those skilled in the art can certainly contemplate a variety of different procedures in which the present invention can be advantageously applied.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

I claim:

1. An interference screw driver assembly for securing an interference screw in surgery, the screw driver assembly comprising:
    a rigid guide pin having a proximal end, a distal end and a cylindrical exterior shape;
    a driver having a proximal end and a distal end;
    a pin connection means to directly connect the rigid guide pin to the driver;
    an interference screw having a longitudinal bore whereby at least a portion of the rigid guide pin and the driver can be received in the screw longitudinal bore;
    a handle having a longitudinal axis, a fore handle and a rear handle;
    the rear handle configured to receive a forward force from a proximal end of the interference screw driver assembly and provide the forward force to the rigid guide pin and the interference screw;
    the forward force directed from the proximal end of the interference screw driver assembly toward the rigid guide pin;
    the rear handle positioned between the proximal end of the interference screw driver assembly and the fore handle;
    the rear handle connected to the fore handle whereby the rear handle rotates about the longitudinal axis without rotating the driver;
    the fore handle configured to receive a rotational force and provide the rotational force to the guide pin and the interference screw;
    the fore handle having a handle connection means to connect the driver to the handle whereby the rigid guide pin and the interference screw can be guided by manipulation of the handle;
    the interference screw further comprising a proximal end and a distal end;
    the interference screw distal end having a size of the longitudinal bore slightly larger than the outside diameter of the rigid guide pin whereby the proximal end of the rigid guide pin can be received in the longitudinal bore of the interference screw distal end; and
    the interference screw proximal end having a size of the longitudinal bore slightly larger than an outside profile of the driver whereby the distal end of the driver can be received in the longitudinal bore of the interference screw proximal end.

2. The interference screw driver assembly of claim 1 wherein the pin connection means comprises:
    the driver distal end having a threaded recess; and
    the rigid guide pin proximal end having threads whereby the threads of the rigid guide pin proximal end are received and mate with the threaded recess of the driver distal end to connect the rigid guide pin with the driver.

3. The interference screw driver assembly of claim 1 wherein the handle connection means comprises:
    the handle having a proximal end, a distal end and a longitudinal axis;
    the distal end of the handle having a recess shaped to receive the proximal end of the driver;
    the handle, the driver and the guide pin being rotationally fixed whereby a rotation of the handle about the longitudinal axis with an engaging force turns the rigid guide pin and the driver about the longitudinal axis and the interference screw can engage a tissue.

4. The interference screw driver assembly of claim 1 wherein:
    the interference screw driver assembly further comprises a shaft; and
    the handle connection means comprises:
        the handle having a proximal end, a distal end and a longitudinal axis,
        the distal end of the handle having a recess shaped to receive a proximal end of the shaft, and
        the shaft further having a distal end shaped to receive the proximal end of the driver whereby a rotation of the handle about the longitudinal axis turns the shaft, the rigid guide pin and the driver about the longitudinal axis.

5. The interference screw driver assembly of claim 1 wherein:
    the rigid guide pin is connected to the driver;
    the driver is connected to the handle; and
    the longitudinal axis of the handle rigidly aligns with a longitudinal axis of the driver and a longitudinal axis of the rigid guide pin.

6. The interference screw driver assembly of claim 1 wherein the assembly is capable of anchoring the interference screw and a ligament in bone.

7. The interference screw driver assembly of claim 1 wherein the screw driver assembly further comprises an additional driver, the additional driver having a different shaped distal end from the driver distal end whereby the driver distal end removably mates to the interference screw and the different shaped distal end removably mates to a second interference screw.

8. The interference screw driver assembly of claim 1 wherein the distal end of the rigid guide pin is configured to extend outside of the longitudinal bore of the interference screw when the rigid guide pin is directly connected to the driver and a portion of the rigid guide pin is inside of the longitudinal bore.

9. The interference screw driver assembly of claim 1 wherein the handle connection means removably connects the driver to the handle.

10. A method of deploying an interference screw comprising the steps of:
    providing an interference screw driver assembly comprising:

a. a rigid guide pin having a proximal end and a distal end,
b. the rigid guide pin terminating at the proximal end of the rigid guide pin,
c. a driver having a proximal end and a distal end,
d. the distal end of the driver shaped to mate with the interference screw;
e. a pin connection means to directly connect the proximal end of the rigid guide pin to the driver,
f. the distal end of the rigid guide pin configured to extend outside of a longitudinal bore in the interference screw when the rigid guide pin is directly connected to the driver and a portion of the rigid guide pin is inside of the bore,
g. a handle having a handle connection means to connect the driver to the handle whereby the rigid guide pin can be guided into a position by positioning the rigid guide pin through manipulation of the handle,
h. the interference screw comprising:
1. a proximal end and a distal end and the longitudinal bore,
2. the interference screw distal end having a size of the longitudinal bore slightly larger than the outside diameter of the rigid guide pin whereby the proximal end of the rigid guide pin can be received in the longitudinal bore of the interference screw distal end, and
3. the interference screw proximal end having a size of the longitudinal bore slightly larger than an outside profile of the driver whereby the distal end of the driver can be received in the longitudinal bore of the interference screw proximal end;
connecting the proximal end of the driver to a distal end of the handle;
connecting the proximal end of the rigid guide pin to the distal end of the driver;
inserting the driver and the rigid guide pin into the longitudinal bore in the interference screw;
driving the rigid guide pin and the interference screw between a graft and a tissue of a patient by manipulating the handle;
anchoring the graft to the tissue with the interference screw; and
removing the driver and the rigid guide pin from the screw.

11. The method of claim 10 wherein the graft is a previously cut bone block and the tissue is a bone mass having a graft tunnel.

12. The method of claim 10 wherein:
the proximal end of the rigid guide pin is threaded, wherein the step of connecting the rigid guide pin to the driver comprises threading the threaded proximal end of the rigid guide pin into a threaded recess in the driver distal end; and
the step of removing the driver and the rigid guide pin further comprises rotating the rigid guide pin out of the threaded recess in the driver distal end and removing the driver from the interference screw by applying a retrograde force to the driver.

13. The method of claim 10 wherein the step of connecting the proximal end of the driver to the handle further comprises:
selecting a selected driver from a plurality of drivers; and
the plurality of drivers each having a different shape distal end whereby the distal end of the selected driver removably mates to one of a plurality of interference screws.

14. The method of claim 10 wherein the interference screw anchors a ligament in bone.

15. The method of claim 10 wherein the handle connection means removably connects the driver to the handle.

16. A combination of an interference screw driver assembly and an interference screw, wherein the interference screw driver assembly is for securing the interference screw in surgery, wherein:
the screw driver assembly comprises:
a rigid guide pin having a proximal end and a distal end;
a driver having a proximal end and a distal end;
a pin connection means to directly connect the rigid guide pin to the driver;
a handle having a longitudinal axis, a fore handle and a rear handle;
the rear handle configured to receive a forward force and provide the forward force to the guide pin and the interference screw;
the rear handle connected to the fore handle whereby the rear handle rotates about the longitudinal axis without rotating the driver;
the fore handle configured to receive a rotational force and provide the rotational force to the guide pin and the interference screw;
the fore handle having a handle connection means to connect the driver to the handle whereby the rigid guide pin and the interference screw can be guided by manipulation of the handle;
the rigid guide pin having an outside diameter;
the driver having an outside profile;
the pin connection means connects the rigid guide pin to the driver; and
the interference screw comprises:
a longitudinal bore whereby at least a portion of the rigid guide pin and the driver can be received in the screw longitudinal bore;
the interference screw having a proximal end and a distal end;
the interference screw distal end having a size of the longitudinal bore slightly larger than the outside diameter of the rigid guide pin; and
the interference screw proximal end having a size of the longitudinal bore slightly larger than the driver outside profile whereby the proximal end of the rigid guide pin can be received in the longitudinal bore of the interference screw distal end and the distal end of the driver can be received in the longitudinal bore of the interference screw proximal end.

17. A combination of an interference screw driver assembly and an interference screw, wherein the interference screw driver assembly is for securing the interference screw in surgery, wherein:
the screw driver assembly comprises:
a rigid guide pin having a proximal end and a distal end;
the rigid guide pin terminating at the proximal end of the rigid guide pin;
a driver having a proximal end and a distal end;
the distal end of the driver shaped to mate with the interference screw;
a pin connection means to directly connect the proximal end of the rigid guide pin to the driver;
the distal end of the rigid guide pin configured to extend outside of a longitudinal bore in the interference screw when the rigid guide pin is directly connected to the driver;
a handle having a handle connection means to connect the driver to the handle whereby the rigid guide pin can be guided into a position by positioning the rigid guide pin through manipulation of the handle; and the interference screw comprises:
- a proximal end, a distal end and the longitudinal bore;
- the interference screw distal end having a size of the longitudinal bore slightly larger than an outside diameter of the rigid guide pin whereby the proximal end of the rigid guide pin can be received in the longitudinal bore of the interference screw distal end; and
- the interference screw proximal end having a size of the longitudinal bore slightly larger than an outside profile of the driver whereby the distal end of the driver can be received in the longitudinal bore of the interference screw proximal end.

18. The interference screw driver assembly of claim 17 wherein the handle connection means removably connects the driver to the handle.

19. The interference screw driver assembly of claim 17 wherein the assembly is capable of anchoring the interference screw and a ligament in bone.

20. The interference screw driver assembly of claim 17 further comprising an additional driver, the additional driver having a different shaped distal end from the driver distal end whereby the driver and the additional driver can be interchanged and the driver distal end can mate to the interference screw and the different shaped distal end can mate to a second interference screw.

21. The interference screw driver assembly of claim 17 wherein the pin connection means comprises:
- the driver distal end having a threaded recess; and
- the rigid guide pin proximal end having threads whereby the threads of the rigid guide pin proximal end are received and mate with the threaded recess of the driver distal end to connect the rigid guide pin with the driver.

* * * * *